US007550550B2

United States Patent
Klein et al.

(10) Patent No.: US 7,550,550 B2
(45) Date of Patent: Jun. 23, 2009

(54) POLYETHER POLYAMINE AGENTS AND MIXTURES THEREFOR

(75) Inventors: Howard P. Klein, Austin, TX (US); Bruce L. Burton, Round Rock, TX (US); Matthew W. Forkner, Austin, TX (US); David C. Alexander, Austin, TX (US); Terry L. Renken, Austin, TX (US); Chris E. Godinich, Houston, TX (US)

(73) Assignee: Huntsman Petrochemical Corporation, The Woodlands, TX (US)

( * ) Notice: Subject to any disclaimer, the term of this patent is extended or adjusted under 35 U.S.C. 154(b) by 333 days.

(21) Appl. No.: 10/524,247

(22) PCT Filed: Aug. 29, 2003

(86) PCT No.: PCT/US03/27082

§ 371 (c)(1),
(2), (4) Date: Feb. 10, 2005

(87) PCT Pub. No.: WO2004/020506

PCT Pub. Date: Mar. 11, 2004

(65) Prior Publication Data

US 2005/0234216 A1 Oct. 20, 2005

Related U.S. Application Data

(60) Provisional application No. 60/409,492, filed on Sep. 10, 2002, provisional application No. 60/407,112, filed on Aug. 30, 2002.

(51) Int. Cl.
*C08G 18/32* (2006.01)
(52) U.S. Cl. .................. 528/68; 528/419; 564/508; 564/505
(58) Field of Classification Search .................. 528/68, 528/419; 564/508, 505
See application file for complete search history.

(56) References Cited

U.S. PATENT DOCUMENTS

| 3,654,370 | A | * | 4/1972 | Yeakey | 564/480 |
| 4,178,427 | A | * | 12/1979 | Waddill et al. | 528/124 |
| 4,487,806 | A | * | 12/1984 | Sellstrom et al. | 428/413 |
| 4,814,415 | A | | 3/1989 | Sellstrom et al. | |

FOREIGN PATENT DOCUMENTS

EP 0329266 8/1989

* cited by examiner

*Primary Examiner*—Margaret G Moore
(74) *Attorney, Agent, or Firm*—Ron D. Brown; Edward Korompal

(57) ABSTRACT

Provided herein are polyamine precursors useful in the manufacture of epoxy resins. Use of a polyamine precursor according to the invention provides an epoxy resin formulation having an increased working time over prior art amines used for curing epoxies. Increased working times translate to the ability to manufacture composites which could not be made using conventional epoxy curing agents, such as composite blades for wind-driven turbines. Such polyamines are also useful in polyurea formulations for lengthening reaction time, thus allowing more flow of applied polyurea coatings prior to gellation.

8 Claims, No Drawings

POLYETHER POLYAMINE AGENTS AND MIXTURES THEREFOR

CROSS-REFERENCES TO RELATED APPLICATIONS

This application claims the benefit of U.S. Provisional Application No. 60/407,112 filed Aug. 30, 2002, and U.S. Provisional Application No. 60/409,492 filed Sep. 10, 2002, which are both currently still pending, the entire contents of each of which are herein incorporated fully by reference thereto.

FIELD OF THE INVENTION

The present invention relates to epoxy resins. More particularly it relates to amine curing agents useful in curing epoxy resins. More particularly still, the invention relates to amine curing agents which display reduced reactivity as a curing agent, which translates to an increased "working time" associated with the manufacture of articles from epoxy resins.

BACKGROUND INFORMATION

Manufacturing processes commonly used in conjunction with the production of epoxies include filament winding, pultrusion, infusion molding, resin transfer molding (RTM), vacuum assisted RTM (VARTM), and wet lay-up or vacuum bag techniques. Polyoxyalkylene amines, or "polyetheramines" as they are sometimes called, are useful as curing agents in epoxy systems to improve flexibility, and to lengthen working time in the manufacture of fiber-reinforced composites. The "working time" is defined as the time period between when the reactive components of the epoxy resin are first mixed with one another and when the mixture is no longer suitable for processing. During the working time, the resin or article containing the resin remains in a pourable, flexible, pliable or otherwise mouldable form.

The use of epoxy binders is preferred by many manufacturers of fiber-reinforced composite wind turbine generator ("WTG") propellers, which propellers each typically comprise three individual epoxy-composite blades having lengths from 20-40 meters each. Unfortunately, the working times provided for by currently-available amine curing agents are insufficient for the preparation of blades having optimal properties. In addition to a longer working time, the materials from which a WTG blade material is made must also maintain good heat resistance when cured.

Many WTG blade manufacturers today use the VARTM process when working with liquid epoxy systems or epoxy polyester systems. These resin systems must cure slowly in a controlled fashion and allow sufficient working time to wet-out the fiberglass, aramid fiber, carbon fiber, or other fibers that are used as reinforcing materials in the wind turbine blades. In some cases, prepreg epoxy systems may be used. In these instances, fibers pre-impregnated with a reasonably latent epoxy resin system may be used to form the turbine blade. The use of polyetheramines as epoxy curing agents is not common in the prepreg materials, but is common practice by some using VARTM and other liquid molding processes, where JEFFAMINE® D-230 amine (Huntsman Corporation, Houston, Tex.) is used in large quantities. However, manufacturers understand that the working time for using such materials is too short for optimum production, mainly when manufacturing individual blades of greater than 30 meters in length. Since the tendency in the WTG industry is to go to longer blade length to increase the ability of each WTG to produce more power/unit, a need has arisen in the art for curing agents which can make the manufacture of such blades commercially viable.

SUMMARY OF THE INVENTION

The present invention provides polyamines useful as a curing agent in epoxy resins having the structure:

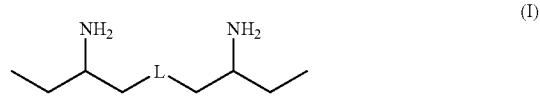

(I)

wherein L is an oxyalkoxo group having the structure:

—O—$R_1$—O— (II)

in which $R_1$ is any group selected from the group consisting of: $C_1$ to $C_5$ alkylene; 2-methyl propylene; 2,2-dimethyl propylene; —$CH_2CH_2$—O—$CH_2CH_2$—; —$CH_2CH_2CH_2$—O—$CH_2CH_2CH_2$—; the group

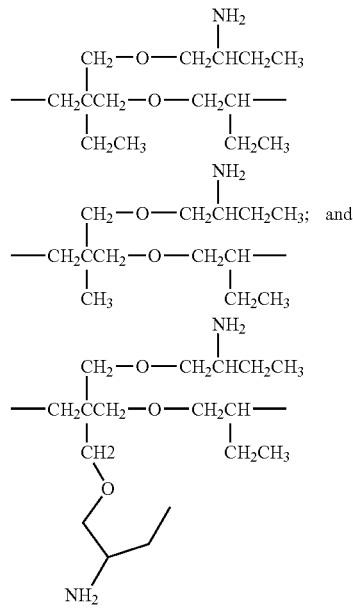

The invention also includes a process for. preparing a cured epoxy resin comprising the steps of: a) providing a polyamine per the above, or mixtures thereof with each other or with one or more materials selected from the group consisting of: N-aminoethylpiperazine; diethylenetriamine; triethylenetetramine; tetraethylenepentamine; 2-methylpentamethylene;1, 3-pentanediamine; trimethylhexamethylene diamine; a polyamide; a polyamidoamine; a Mannich-base type hardener; bis(aminomethyl)cyclohexylamine; isophorone diamine; menthane diamine; bis(p-aminocyclohexyl)methane; 2,2'-dimethyl bis(p-aminocyclohexyl)methane; dimethyldicyclohexylmethane); 1,2-diaminocyclohexane; 1,4-diaminocyclohexane; meta-xylene diamine; norbomanediamine; meta-phenylene diamine; diaminodiphenylsulfone; methylene dianiline; JEFFAMINE® D-230; JEFFAMINE® D-400; JEFFAMINE® T-403; and diethyltoluenediamine;

b) providing an epoxy precursor comprising a material having at least two epoxy end groups; and
c) contacting said epoxy precursor and said polyamine with one another.

Suitable polyfunctional epoxy precursors are those which have at least two epoxy end groups and include the following:

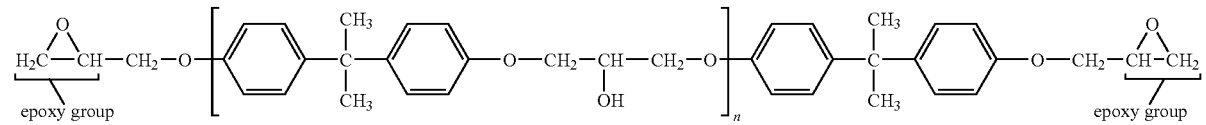

in which n may be any integer between 0 and about 4; DGEBF (diglycidylether of bisphenol F) having the following structure:

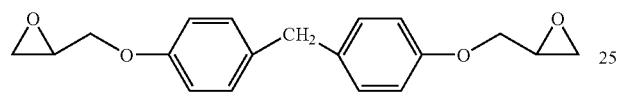

such as D.E.R.(R) 354 epoxy resin from The Dow Chemical Company; and tri-functional epoxy resins such as TACTIX (R) 742 epoxy from Huntsman Applied Materials:

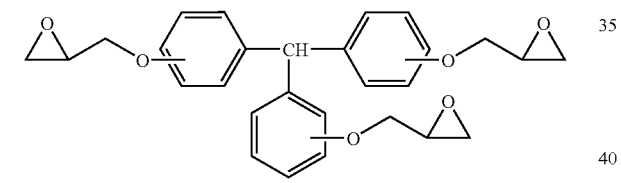

Higher functional epoxy resins such as epoxy novolacs (D.E.N.® 438 epoxy resin, ARALDITE® EPN 1180 epoxy NOVOLAC D.E.N.® 431 epoxy resin are also suitable for use in a process according to the present invention. All materials which contain at least two epoxy groups in their molecular structure are suitable for use in this invention, including without limitation those described above, and such materials are conveniently referred to as "polyfunctional epoxy precursor" in the claims appended hereto.

DETAILED DESCRIPTION OF THE INVENTION

This invention involves the preparation of hindered polyetheramines. It also relates to the use of hindered polyetheramines for curing standard epoxy resins. An epoxy resin cured using a polyetheramine according to the invention has a longer working time those made using prior art amine curing agents.

The present invention provides primary polyetherdiamines and polyethertriamines which are preferably prepared by reductive amination of alcohols such as those in formulae (III)-(XI) below:

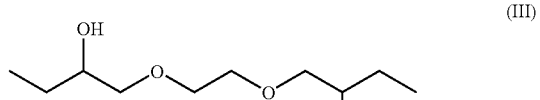
(III)

(IV)

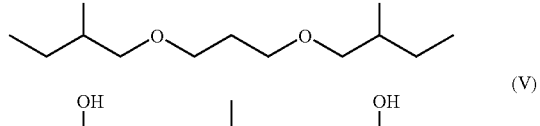
(V)

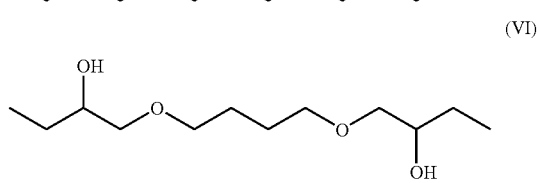
(VI)

(VII)

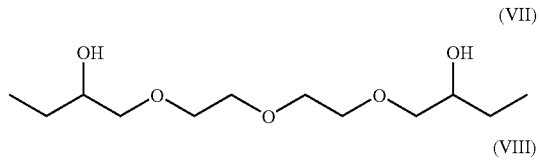
(VIII)

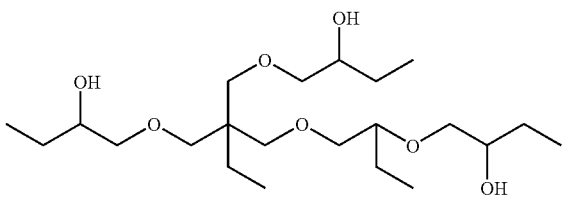
(IX)

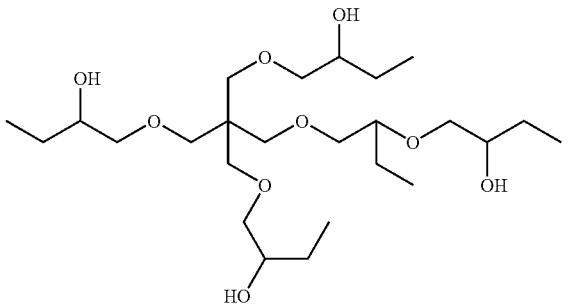

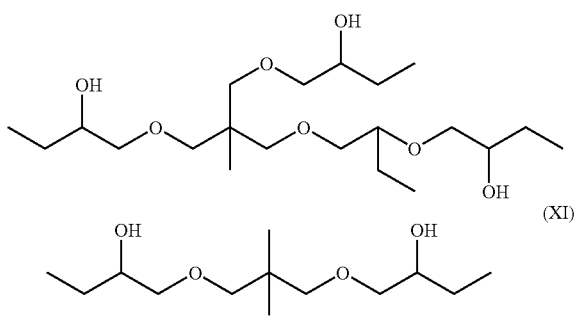

(X)

(XI)

According to one preferred form of the invention, a polyol according to those specified in formulae (III)-(XI) is first prepared via alkoxylation of a suitable initiator. The reaction may be carried out by heating the initiator and the corresponding higher alkyl-substituted oxirane in a closed reaction vessel at relatively low pressures. Reaction temperatures of 100-110° C. are used in the presence of a base catalyst, such as a tertiary amine or alkali metal hydroxide for several hours. Then the mixture is vacuum stripped of any excess unreacted oxirane and the catalyst to leave the resulting polyol mixture. It is preferred that polyols of the invention be prepared wholly or partially from oxiranes, having alkyl groups with carbon numbers of $C_2$ to $C_{10}$. The alkyl group may be branched or linear in structure. One preferred and more readily available oxirane in this class is 1,2-butylene oxide, which may be self-polymerized with base catalysts, using water as an initiator, to produce low-molecular weight polyoxybutylene diols or glycerin as an initiator to produce similar triols of 200-400 MW. Polyols with larger pendant alkyl groups would have more steric crowding about the mainly secondary hydroxyl groups at the end of the polyol chains. A mixture of oxiranes may also be used in the process of polyol preparation, but the oxirane of higher alkyl substitution should be added on to the end of each polyol chain prior to the neutralization and reductive amination steps. Examples of other oxiranes to be used in the internal polyol backbone are ethylene oxide and propylene oxide. Thus, the starting materials for the polyol precursors of the polyamines of the invention may consist of 1,2-glycols, such as ethylene glycol and propylene glycol, or higher diols, such as diethylene glycol or dipropylene glycol. In addition, longer carbon chain diols, such as 1,3-propanediol, 1,4-butanediol or 1,6-hexanediol may be used as starting material for the addition of the higher oxirane to prepare the hindered polyols for reductive amination to the hindered polyetheramines. Multifunctional initiators, such as glycerin, trimethylol- propane (TMP), pentaerythritol, and alpha methyl glucoside (AMG), may also be alkoxylated with the higher oxiranes to prepare polyols for reductive amination. After neutralization, the polyols may be purified by distillation, and subsequently aminated reductively in the presence of hydrogen and excess ammonia at pressures up to 2000 psi and temperatures about or in excess of 200° C. using a suitable metal catalyst as described by Yeakey et al. 1). Examples of the preferred preparatory methods for these polyols are now set forth.

Polyol (Formula III)-Ethylene Glycol+Butyleneoxide

To a dry, nitrogen purged reactor were added 2500 grams of ethylene glycol and 12.5 grams of 1,1,3,3-tetramethylguanidine (TMG). 5809 grams butyleneoxide were then added while agitating. The kettle was then heated to 80° C. and temperature control was initiated. The kettle was then held at 80° C. for 10 hours, followed by an additional 10 hours at 100° C. The product was then stripped for one hour at 100° C. using nitrogen and the product was then collected. The reaction was followed by gas chromatography during the process.

Polyol (Formula IV)-Propanediol+Butyleneoxide

To a dry, nitrogen purged reactor were added 2500 grams of propanediol and 12.5 grams of 1,1,3,3,-tetramethylguanidine (TMG). 4270 grams butyleneoxide were then added while agitating. The kettle was then heated to 80° C. and temperature control was initiated. The kettle was then held at 80° C. for 10 hours, followed by an additional 10 hours at 100° C. The product was then stripped for one hour at 100° C. using nitrogen and the product was then collected. The reaction was followed by gas chromatography during the process.

Polyol (Formula V)-2-Methyl-1,3-Propanediol+Butyleneoxide

To a dry, nitrogen purged reactor were added 2000 grams of 2-methyl-1,3-propanediol and 10.0 grams of 1,1,3,3,-tetramethylguanidine (TMG). 3361 grams butyleneoxide were then added while agitating. The kettle was then heated to 80° C. and temperature control was initiated. The kettle was then held at 80° C. for 10 hours, followed by an additional 10 hours at 100° C. The product was then stripped for one hour at 100° C. using nitrogen and the product was then collected. The reaction was followed by gas chromatography during the process.

Polyol (Formula VI)-1,4-Butanediol+Butyleneoxide

To a dry, nitrogen purged reactor were added 3000 grams of 1,4-butanediol and 30.0 grams of potassium hydroxide as catalyst. 4321 grams butyleneoxide were then added while agitating. The kettle was then heated to 80° C. and temperature control was initiated. The kettle was then held at 80° C. for 10 hours, followed by an additional 10 hours at 100° C. The product was then stripped for one hour at 100° C. using nitrogen and the product was then collected. The reaction was followed by gas chromatography during the process.

Polyol (Formula VII)-Diethylene Glycol+Butyleneoxide

To a dry, nitrogen purged reactor were added 2500 grams of diethylene glycol and 12.5 grams of 1,1,3,3,-tetramethylguanidine (TMG). 2973 grams butyleneoxide were then added while agitating. The kettle was then heated to 80° C. and temperature control was initiated. The kettle was then held at 80° C. for 10 hours, followed by an additional 10 hours at 100° C. The product was then stripped for one hour at 100° C. using nitrogen and the product was then collected. The reaction was followed by gas chromatography during the process.

Polyol (Formula VIII)-Trimethylolpropane+Butyleneoxide

To a dry, nitrogen purged reactor were added 2268 grams of 1,1,1-trimethylolpropane and 11.34 grams of 1,1,3,3,-tetramethylguanidine (TMG) as catalyst. 4266 grams butyleneoxide were then added while agitating. The kettle was then heated to 80° C. and temperature control was initiated. The kettle was then held at 80° C. for 10 hours, followed by an additional 10 hours at 100° C. The product was then stripped for one hour at 100° C. using nitrogen and the product was then collected. The reaction was followed by gas chromatography during the process.

Polyol (Formula X)-Tris(Hydroxymethyl)Ethane+Butyleneoxide

To a dry, nitrogen purged reactor were added 2500 grams of tris(hydroxymethyl)ethane and 12.5 grams of 1,1,3,3,-tetramethylguanidine (TMG). 6002 grams butyleneoxide were then added while agitating. The kettle was then heated to 80° C. and temperature control was initiated. The kettle was then held at 80° C. for 10 hours, followed by an additional 10 hours at 100° C. The product was then stripped for one hour at 100° C. using nitrogen and the product was then collected. The reaction was followed by gas chromatography during the process.

Conversion of Butoxylates to Amines

The polyols in formulas (III)-(XI) above were reductively aminated using ammonia to the corresponding amines in a 100 cc continuous unit using a catalyst as described in U.S. Pat. Nos. 3,151,112 and 3,654,370. The catalyst, in the form of ⅛×⅛ inch tablets, was charged to the 100 cc tubular reactor. The polyol and ammonia were pumped separately and mixed in-line with hydrogen and fed through the catalyst bed. The polyol and ammonia were kept in an approximate 1:1 wt feed ratio, while the ammonia to hydrogen mole ratio was kept at about 20:1. The reactor pressure was held at about 2000 psig and the temperature was maintained at about 220° C. The polyol and ammonia feed rates used in each run varied between about 65 g/hr to 100 g/hr. The products were collected over 2-3 days and stripped of excess ammonia, water and light amines. In some of the amination runs, the material was passed through the reactor a second time to bring up the amine level in the product. Reductive amination of these polyols yields the polyamines having predominantly the structures shown below in formulae (XII)-(XX) below:

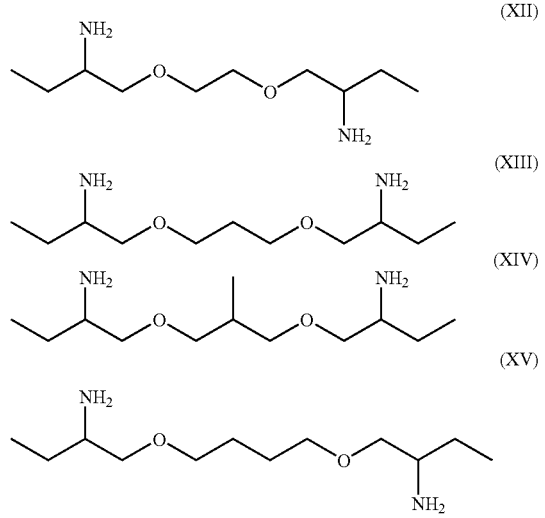

(XII)

(XIII)

(XIV)

(XV)

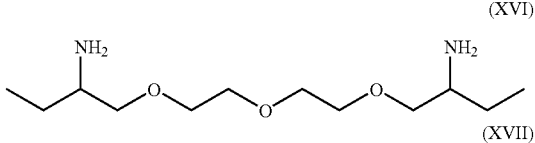

(XVI)

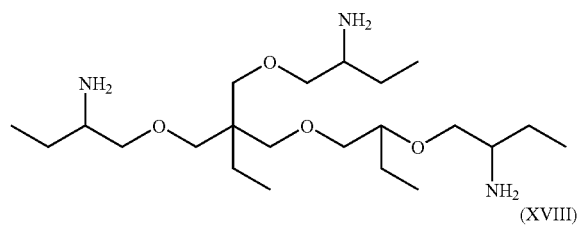

(XVII)

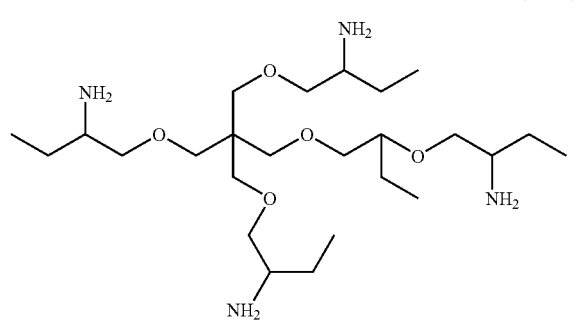

(XVIII)

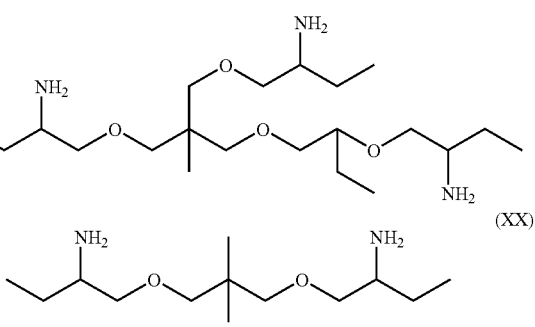

(XIX)

(XX)

Thus, the polyamine of formula XII is represented by formulas (I) and (II) wherein $R_1$ is an ethylene group. The polyamine of formula XIII is represented by formulas (I) and (II) wherein $R_1$ is a propylene group. The polyamine of formula XIV is represented by formulas (I) and (II) wherein $R_1$ is a 2-methyl propylene group. The polyamine of formula XV is represented by formulas (I) and (II) wherein $R_1$ is a butylene group. The polyamine of formula XVI is represented by formulas (I) and (II) wherein $R_1$

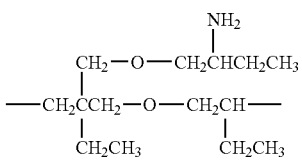

is a —CH2CH2—O—CH2CH2—group. The polyamine of formula XVII is represented by formulas (1) and (II) wherein $R_1$ is a group.

The polyamine of formula XVIII is represented by formulas (I) and (II) wherein $R_1$ is a

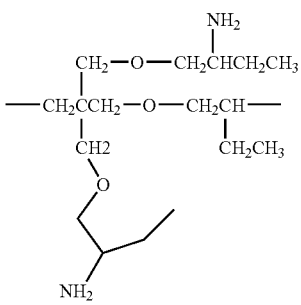

group. The polyamine of formula XIX is represented by formulas (I) and (II) wherein $R_1$ is a

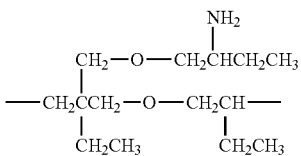

group. The polyamine of formula XX is represented by formulas (I) and (II) wherein $R_1$ is a 2,2-dimethyl propylene group.

The gel times of an epoxy blend are longer for amines having ethyl groups on the carbon atom alpha to the amine vs. those having methyl groups on the carbon atom alpha to the amine. The polyetheramines of the invention offer more than 50% longer working time, when used to cure standard epoxy resins than is afforded using amine curing agents of the prior art. We were surprised to find that some of the polyetheramines took almost twice as long to cure epoxy resins as the standard products now used in the current wind blade manufacture, specifically, the amine of formula XIV.

Conditions useful for preparing a composition relating to the present invention include: A temperature range of 50-120° C. for the polyol preparations; and 180-220° C. for the reductive amination of polyols. The useful pressures are: 40-100 psi for the polyol preparations, and 1500-2500 psi for the reductive aminations.

A polyamine according to the formulas (XII) through (XX) can be reacted with an organic di-isocyanate to form a polyurea. These di-isocyanates include standard isocyanate compositions known to those skilled in the art. Preferred examples of di-isocyanates include MDI-based quasi prepolymers such as those available commercially as RUBINATE® 9480, RUBINATE® 9484, and RUBINATE® 9495 from Huntsman International, LLC. Liquified MDI such as MONDUR® ML may be used as all or part of the isocyanate. The isocyanates employed in component (A) are generally known to one skilled in the art. Thus, for instance, they can include aliphatic isocyanates of the type described in U.S. Pat. No. 4,748,192. Accordingly, they are typically aliphatic diisocyanates and, more particularly, are the trimerized or the biuretic form of an aliphatic diisocyanate, such as hexamethylene diisocyanate, or the bifunctional monomer of the tetraalkyl xylene diisocyanate, such as the tetramethyl xylene diisocyanate. Cyclohexane diisocyanate is also to be considered a preferred aliphatic isocyanate. Other useful aliphatic polyisocyanates are described in U.S. Pat. No. 4,705,814 which is fully incorporated herein by reference thereto. They include aliphatic diisocyanates, for example, alkylene diisocyanates with 4 to 12 carbon atoms in the alkylene radical, such as 1,12-dodecane diisocyanate and 1,4-tetramethylene diisocyanate. Also described are cycloaliphatic diisocyanates, such as 1,3 and 1,4-cyclohexane diisocyanate as well as any desired mixture of these isomers, 1-isocyanato-3,3,5-trimethyl-5-isocyanato metbylcyclohexane (isophorone diisocyanate); 4,4'-,2,2'- and 2,4'-dicyclohexylmethane diisocyanate as well as the corresponding isomer mixtures, and the like. Further, a wide variety of aromatic polyisocyanates may be used to form the foamed polyurea elastomer of the present invention. Typical aromatic polyisocyanates include p-phenylene diisocyanate, polymethylene polyphenylisocyanate, 2,6-toluene diisocyanate, dianisidine diisocyanate, bitolylene diisocyanate, naphthalene-1,4-diisocyanate, bis(4-isocyanatophenyl) methane, bis(3-methyl-3-iso-cyanatophenyl)methane, bis(3-methyl-4-isocyanatophenyl)methane, and 4,4'-diphenylpropane diisocyanate. Other aromatic polyisocyanates used in the practice of the invention are methylene-bridged polyphenyl polyisocyanate mixtures which have a functionality of from about 2 to about 4. These latter isocyanate compounds are generally produced by the phosgenation of corresponding methylene bridged polyphenyl polyamines, which are conventionally produced by the reaction of formaldehyde and primary aromatic amines, such as aniline, in the presence of hydrochloric acid and/or other acidic catalysts. Known processes for preparing polyamines and corresponding methylene-bridged polyphenyl polyisocyanates therefrom are described in the literature and in many patents, for example, U.S. Pat. Nos. 2,683,730; 2,950,263; 3,012,008; 3,344,162 and 3,362,979, all of which are fully incorporated herein by reference thereto. Usually, methylene-bridged polyphenyl polyisocyanate mixtures contain about 20 to about 100 weight percent methylene diphenyldiisocyanate isomers, with the remainder being polymethylene polyphenyl diisocyanates having higher functionalities and higher molecular weights. Typical of these are polyphenyl polyisocyanate mixtures containing about 20 to about 100 weight percent diphenyldiisocyanate isomers, of which about 20 to about 95 weight percent thereof is the 4,4'-isomer with the remainder being polymethylene polyphenyl polyisocyanates of higher molecular weight and functionality that have an average functionality of from about 2.1 to about 3.5. These isocyanate mixtures are known, commercially available materials and can be prepared by the process described in U.S. Pat. No. 3,362,979. A preferred aromatic polyisocyanate is methylene bis(4-phenylisocyanate) or "MDI". Pure MDI, quasi-prepolymers of MDI, modified pure MDI, etc. are useful to prepare a polyurea according to the invention. Since pure MDI is a solid and, thus, often inconvenient to use, liquid products based on MDI or methylene bis(4-phenylisocyanate) are used herein. U.S. Pat. No. 3,394,164, incorporated herein by reference thereto, describes a liquid MI product. More generally, uretonimine modified pure MDI is included also. This product is made by heating pure distilled MDI in the presence of a catalyst. The liquid product is a mixture of pure MDI and modified MDI. The term isocyanate also includes quasi-prepolymers of isocyanates or polyisocyanates with active hydrogen containing materials. "Organic diisocyanate" as used herein includes all of the foregoing isocyanates.

In addition to the use of the pure polyamines shown above in formulae (XII)-(XX), the present invention contemplates the use of these amines in each combinations with one another, and with amines of the prior art. Amines of the prior art useful in combination with those of formulae (XII)-(XX) include, without limitation: N-aminoethylpiperazine ("AEP"); diethylenetriamine ("DETA"); triethylenetetramine ("TETA"); tetraethylenepentamine ("TEPA"); 2-methylpentamethylene diamine (Dytek® A—DuPont);1,3-pentanediamine (Dytek®EP—DuPont); trimethylhexamethylene diamine (1:1 mix of 2,2,4-, and 2,4,4-isomers is called Vestamin® TMD—Creanova); polyamide hardeners; polyamidoamine hardeners; Manniche-base type hardeners; bis(aminomethyl)cyclohexylamine ("1,3-BAC"); isophorone diamine ("IPDA"); menthane diamine; bis(p-aminocyclohexyl)methane ("PACM"); 2,2'-dimethyl bis(p-aminocyclohexyl)methane ("DMDC");dimethyldicyclohexylmethane); 1,2-diaminocyclohexane ("DACH"); 1,4-diaminocyclohexane ("DACH"); meta-xylene diamine ("m-XDA"); norbornanediamine ("NBDA"); meta-phenylene diamine ("m-PDA"); diaminodiphenylsulfone ("DDS" or "DADS"); methylene dianiline ("MDA"); JEFFAMINE® D-230 (Huntsman); JEFFAMINE® D-400 (Huntsman); JEFFAMINE® T-403 (Huntsman); and diethyltoluenediamine ("DETDA").

The amines, combinations, and processes provided herein are particularly beneficial in providing epoxy systems having an increased cure time over compositions and processes of the prior art. During the manufacture of particular composite articles, such as wind turbine blades, a long curing time is desirable in order to enable the actively curing resin to penetrate the interstices of the fibers which are part of the composite, while also permitting enough time for molding to place all the material in its desired location. It is often desirable for the resin/catalyst mixture to remain at a viscosity of less than 1000 centipoise at 25 degrees C. for 8 hours.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

What is claimed is:

1. A polyamine composition having the structure:

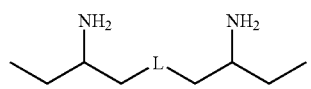
(I)

wherein L is an oxyalkoxo group having the structure:

—O—R$_1$—O— in which R$_1$ comprises at least one of the following:

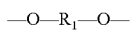

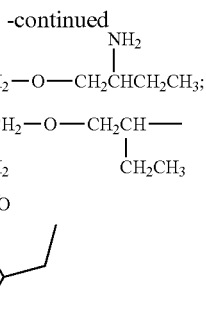

including mixtures of two or more of the foregoing polyamines; wherein the R$_1$ may further comprise a group selected from the group consisting of: C1 to C5 alkylene; 2-methyl propylene; 2,2-dimethyl propylene; —CH2CH2—O—CH2CH2— and —CH2CH2CH2—O—CH2CH2CH2—; including mixtures of two or more of the foregoing polyamines.

2. A process for preparing a cured epoxy (poly-(etheralkanolamine)) resin comprising the steps of:
a) providing a polyamine composition according to claim 1;
b) providing a polyfunctional epoxy precursor; and
c) contacting said polyfunctional epoxy precursor and said polyamine with one another.

3. A process for preparing a polyurea comprising the steps of:
a) providing an organic di-isocyanate;
b) providing at least one polyamine composition according to claim 1; and
c) contacting said organic di-isocyanate and said polyamine with one another.

4. A process for preparing a cured epoxy (poly-(etheralkanolamine)) resin comprising the steps of:
a) providing an amine mixture comprising a polyamine composition according to claim 1, and one or more materials selected from the group consisting of: N-aminoethylpiperazine; diethylenetriamine; triethylenetetramine; tetraethylenepentamine; 2-methylpentamethylene;1,3-pentanediamine; trimethylhexamethylene diamine; a polyamide hardener; a polyamidoamine hardener; a Mannich-base hardener; bis(aminomethyl) cyclohexylamine; isophorone diamine; menthane diamine; bis(p-aminocyclohexyl)methane; 2,2'-dimethyl bis(p-aminocyclohexyl)methane; dimethyldicyclohexylmethane; 1,2-diaminocyclohexane; 1,4-diaminocyclohexane; meta-xylene diamine; norbornanediamine; meta-phenylene diamine; diaminodiphenylsulfone; methylene dianiline; JEFFAMINE® D-230 amine; JEFFAMINE® D-400 amine; JEFFAMINE® T-403 amine; and diethyltoluenediamine;
b) providing an polyfunctional epoxy; and
c) contacting said polyfunctional epoxy precursor and said polyamine with one another.

5. A process for preparing a polyurea comprising the steps of:
a) providing an organic di-isocyanate;
b) providing a polyamine according to claim 1 in admixture with at least one material selected from the group consisting of: N-aminoethylpiperazine; diethylenetriamine; triethylenetetramine; tetraethylenepentam; 2-methylpentamethylene diamine; 1,3-pentanediamine; trimethylhexamethylene diamine; polyamide hardeners; polyamidoamine hardeners; Mannich-base hardeners; bis(aminomethyl) cyclohexylamine; isophorone diamine; menthane diamine; bis(p-aminocyclohexyl)methane ("PACM"); 2,2'-dimethyl bis (p-aminocyclohexyl) methane; dimethyldicyclohexylmethane; 1,2-diaminocyclohexane; 1,4-diaminocyclohexane; meta-xylene; norbornanediamine; meta-phenylene diamine; diaminodiphenylsulfone; methylene dianiline; JEFFAMINE® D-230 amine; JEFFAMINE® D-400 amine; JEFFAMINE® T-403 amine; and diethyltoluenediamine; and c) contacting said organic di-isocyanate and said polyamine with one another.

6. The polyamine composition of claim 1, wherein the $R_1$ further comprises at least one of a $C_1$ to $C_5$ alkylene and mixtures thereof.

7. The polyamine composition of claim 1, wherein the $R_1$ further comprises at least one of 2-methyl propylene; 2,2-dimethyl propylene; and mixtures thereof.

8. The polyamine composition of claim 1, wherein the $R_1$ further comprises at least one of —$CH_2CH_2$—O—$CH_2CH_2$—; —$CH_2CH_2CH_2$—O—$CH_2CH_2CH_2$—; and mixtures thereof.

* * * * *